United States Patent [19]

Siller

[11] Patent Number: 4,490,679
[45] Date of Patent: Dec. 25, 1984

[54] PROBE TYPE PARAFFIN MONITOR
[75] Inventor: David Siller, Houston, Tex.
[73] Assignee: Texaco Inc., White Plains, N.Y.
[21] Appl. No.: 406,618
[22] Filed: Aug. 9, 1982
[51] Int. Cl.³ ............................................. G01N 27/00
[52] U.S. Cl. ..................................... 324/446; 422/68; 436/141; 436/149; 204/412
[58] Field of Search .................. 422/68; 324/439, 442, 324/446, 447, 449, 65 P, 436, 448; 204/406, 412; 436/150

[56] References Cited

U.S. PATENT DOCUMENTS

| | | | |
|---|---|---|---|
| 3,777,257 | 12/1973 | Geisselmann | 324/61 R |
| 3,967,198 | 6/1976 | Gensler | 324/72 |
| 4,112,355 | 9/1978 | Gibson, Jr. et al. | 324/57 R |
| 4,219,776 | 8/1980 | Arulanandan | 324/323 |

Primary Examiner—Barry S. Richman
Assistant Examiner—Joseph P. Carrier
Attorney, Agent, or Firm—Robert A. Kulason; Ronald G. Gillespie

[57] ABSTRACT

A paraffin monitor apparatus responsive to changes in resistance includes a plurality of paraffin sensing means which are placed in a liquid medium containing paraffin. The paraffin sensing means are housed in a non-metallic, hard material having a plurality of channels so that each paraffin sensing means has at least one surface substantially in conformity to a surface of the non-metallic, hard material. A predetermined length of tubing is affixed to the non-metallic, hard material, and a plurality of wires, each of which passes through a channel of the non-metallic, hard material and the tubing, connect with corresponding paraffin sensing means. An adapter affixed to the tubing permits insertion of the non-metallic, hard material and a portion of the tubing into a pipeline containing a flowing liquid medium having paraffin. A manually operative switching device connected to the paraffin monitor apparatus and to the plurality of paraffin sensing means by the plurality of wires allows selection of pairs of paraffin sensing means to be connected to the paraffin monitor apparatus so as to monitor paraffin buildup at different locations in the flowing liquid medium.

3 Claims, 1 Drawing Figure

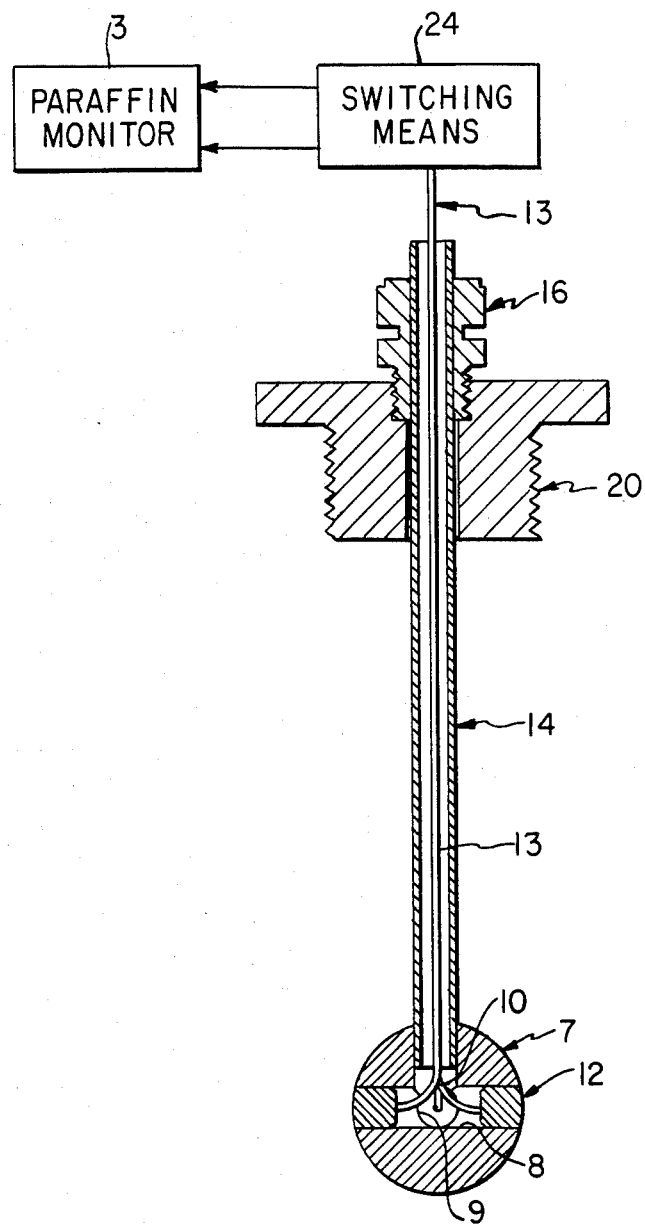

PROBE TYPE PARAFFIN MONITOR

BACKGROUND OF THE INVENTION

Field of the Invention

The present invention relates to monitors in general and, more particularly, to a paraffin monitor.

SUMMARY OF THE INVENTION

A paraffin monitor apparatus responsive to changes in resistance includes a plurality of paraffin sensing means which are placed in a liquid medium containing paraffin. The paraffin sensing means are housed in a non-metallic, hard material having a plurality of channels so that each paraffin sensing means has at least one surface substantially in conformity to a surface of the non-metallic, hard material. A predetermined length of tubing is affixed to the non-metallic, hard material, and a plurality of wires, each of which passes through a channel of the non-metallic, hard material and the tubing, connect with corresponding paraffin sensing means. An adapter affixed to the tubing permits insertion of the non-matallic, hard material and a portion of the tubing into a pipeline containing a flowing liquid medium having paraffin. A manually operative switching device connected to the paraffin monitor apparatus and to the plurality of paraffin sensing means by the plurality of wires allows selection of pairs of paraffin sensing means to be connected to the paraffin monitor apparatus so as to monitor paraffin buildup at different locations in the flowing liquid medium—, The objects and advantages of the invention will appear more fully hereinafter from a consideration of the detailed description which follows, taken together with the accompanying drawing wherein one embodiment of the invention is illustrated by way of example. It is to be expressly understood, however, that the drawing is for illustration purposes and is not to be construed as defining the limits of the invention.

DESCRIPTION OF THE DRAWING

The FIGURE is a simplified drawing of a probe type paraffin monitor constructed in accordance with the present invention.

DESCRIPTION OF THE INVENTION

The present invention represents an improvement over the paraffin monitor of U.S. Pat. No. 4,415,859 issued Nov. 15, 1983, which is shown in the FIGURE as paraffin monitor 3, with the exception of the probes 20 and 22 of that application. The present invention utilizes a single probe including a spherical hard plastic member 7 having two channels 8 and 9 which intersect each other, each channel 8 or 9 passes through member 7. Another channel 10 intersects channels 8 and 9, at their common intersection, but does not pass through member 9. Four metal elements, hereinafter referred to as paraffin sensing means 12, are mounted, one at each surface entrance of channels 8 and 9.

Paraffin sensing means 12 are electrically connected to four wires 13. The surfaces of paraffin sensing means 12 are machined so they conform to the overall surface of the sphere 7. A stainless steel tubing 14 is inserted in hole 10 at one end and has a tube fitting 16 affixed to its other end. A pipe reducer 20 has tube fitting 16 threaded into it, and may be threaded into an opening in a production pipeline. Wires 13 are connected to metal members 12 and pass through tubing 14. When installed in the field, wires 13 are connected to switching means 24 which in turn provides two wires to paraffin monitor 3.

In operation the probe assembly comprising elements 7 through 20 are inserted into a production stream utilizing a hole in the pipeline which is adapted to receive reducer 20. Wires 13 are connected to the switching means 24. This enables paraffin monitor 3 to select between pairs of paraffin sensing means 12 to meet the operating requirements of the paraffin monitor of the aforementioned U.S. application. By proper orientation the operator may select between upstream and downstream and on either side or upstream and adjacent sides or downstream and adjacent sides. By doing so the operator has a greater flexibility in monitoring paraffin inhibitors or dispersants which may vary in their affect due to the flow conditions of the production stream.

The present invention is a paraffin monitor having a single probe with multiple paraffin sensing means, and being capable of switching between any pair of the paraffin sensing means to give a more accurate reading of the effectiveness of a paraffin inhibitor or dispersant used on a production stream.

What is claimed is:

1. A paraffin monitor comprising:
   a plurality of paraffin sensing means for being coated with paraffin when placed in a liquid medium containing paraffin,
   paraffin monitor means for responding to changes in resistance between a pair of the paraffin sensing means,
   a housing made of a non-metallic hard material having channels therein and in which the paraffin sensing means are inserted in a predetermined spatial relationship to each other and so that each paraffin sensing means has at least one surface substantially in conformity to the surface of the housing,
   a predetermined length of tubing affixed to the housing,
   a plurality of wires, each wire passing through a channel of the housing and the tubing and connected to a corresponding paraffin sensing means,
   adapter means affixed to the tubing for permitting insertion of the housing and a portion of the tubing into a pipeline containing a flowing liquid medium having paraffin, and
   manually operative switching means connected to the paraffin monitor means and to the plurality of paraffin sensing means by the wires for monitoring the paraffin build-up on the paraffin sensing means by selecting pairs of paraffin sensing means to be connected to the paraffin monitor means so as to monitor the paraffin build-up at different locations in the flowing liquid medium.

2. A paraffin monitor as described in claim 1 in which the adapter means includes a reducer which may be threaded into an opening in the pipeline, and an adapter affixed to the tubing and having external threads for being threaded into the reducer so as to hold the tubing in place within the pipeline.

3. A paraffin monitor as described in claim 2 in which the non-metallic member is hard plastic.

* * * * *